(12) United States Patent
Okuda

(10) Patent No.: US 11,213,279 B2
(45) Date of Patent: Jan. 4, 2022

(54) ULTRASONIC PROBE AND ULTRASONIC DIAGNOSTIC DEVICE

(71) Applicant: Konica Minolta, Inc., Chiyoda-ku Tokyo (JP)

(72) Inventor: Shuhei Okuda, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 682 days.

(21) Appl. No.: 15/949,490

(22) Filed: Apr. 10, 2018

(65) Prior Publication Data
US 2018/0296195 A1    Oct. 18, 2018

(30) Foreign Application Priority Data

Apr. 12, 2017 (JP) .............................. JP2017-079091

(51) Int. Cl.
*A61B 8/00* (2006.01)
*B06B 1/02* (2006.01)
*B06B 1/06* (2006.01)

(52) U.S. Cl.
CPC ............ *A61B 8/546* (2013.01); *A61B 8/4281* (2013.01); *A61B 8/4405* (2013.01); *A61B 8/4444* (2013.01); *B06B 1/0207* (2013.01); *B06B 1/0622* (2013.01); *B06B 1/0644* (2013.01); *B06B 2201/76* (2013.01)

(58) Field of Classification Search
CPC ..... A61B 8/546; A61B 8/4405; A61B 8/4281; A61B 8/4444; B06B 1/0622; B06B 1/0207; B06B 1/0644; B06B 2201/76
See application file for complete search history.

(56) References Cited

U.S. PATENT DOCUMENTS

| 9,719,968 B2* | 8/2017 | Fujii ..................... A61B 8/4483 |
| 2006/0100513 A1* | 5/2006 | Hashimoto .............. A61B 8/00 600/437 |
| 2008/0306389 A1* | 12/2008 | Nagano .................. A61B 8/546 600/462 |
| 2009/0034370 A1* | 2/2009 | Guo ........................ H04R 31/00 367/180 |

FOREIGN PATENT DOCUMENTS

| JP | H10085219 A | 4/1998 |
| JP | 2000184497 A | 6/2000 |
| JP | 2015503283 A | 1/2015 |

OTHER PUBLICATIONS

JPO Notice of Reasons for Refusal for corresponding JP Application No. 2017-079091; dated Jan. 12, 2021.

* cited by examiner

*Primary Examiner* — Joel Lamprecht
(74) *Attorney, Agent, or Firm* — Cantor Colburn LLP

(57) ABSTRACT

An ultrasonic probe includes: an ultrasonic vibrator that transmits and receives an ultrasonic wave; a wire member that is electrically connected to the ultrasonic vibrator and is provided along a side surface of the ultrasonic vibrator; a shield member that is provided outside the wire member from a viewpoint of the ultrasonic vibrator and electrically protects the ultrasonic vibrator; and a first heat conduction member that is provided in contact with the ultrasonic vibrator, wherein the first heat conduction member and the shield member are thermally connected to each other.

6 Claims, 8 Drawing Sheets

ULTRASONIC PROBE AND ULTRASONIC DIAGNOSTIC DEVICE

The present application claims priority under 35 U.S.C. § 119 to Japanese patent Application No. 2017-079091, filed on Apr. 12, 2017, the entire content of which is incorporated herein by reference.

BACKGROUND

Technological Field

The present invention relates to an ultrasonic probe and an ultrasonic diagnostic device for transmitting and receiving an ultrasonic wave.

Description of the Related Art

Conventionally, ultrasonic diagnostic devices have been widely used to inspect a subject by irradiating an inside of the subject with an ultrasonic wave, and receiving and analyzing a reflection wave thereof. Since the ultrasonic diagnostic devices can inspect the subject in a non-destructive and non-invasive manner, the ultrasonic diagnostic devices have been widely used for various purposes including the medical diagnoses, the inspections of the inside of building structures, and the like.

In general, the ultrasonic diagnostic device includes an ultrasonic probe that irradiates a subject with an ultrasonic wave. The ultrasonic probe includes an ultrasonic vibrator that generates an ultrasonic wave by vibrating when electricity is supplied, an acoustic matching layer that suppresses the reflection of the ultrasonic wave to make it easier to deliver the ultrasonic wave to the subject, and a backing material that suppresses the unnecessary vibration of the ultrasonic vibrator. The acoustic matching layer is disposed close to the subject and the backing material is disposed far from the subject from the viewpoint of the ultrasonic vibrator when the ultrasonic probe is used.

In such an ultrasonic probe, when electricity is supplied to the ultrasonic vibrator, the ultrasonic vibrator vibrates to generate an ultrasonic wave. At the same time as generating the ultrasonic wave, the ultrasonic vibrator also generates heat. If this heat conducts to the acoustic matching layer side, the temperature of an acoustic lens that is a part to be in direct contact with a surface of the subject may increase. Such a temperature increase is not preferable from the aspect of the safety, and therefore, it has been desired to provide an ultrasonic probe with a structure in which the heat generated from the ultrasonic vibrator conducts to the acoustic matching layer side less easily. One example of such an ultrasonic probe is disclosed in JP 2000-184497 A and JP 2015-503283 A.

JP 2000-184497 A discloses an ultrasonic probe including a heat conduction material provided between a piezoelectric element (component of ultrasonic vibrator) and a back-surface load material, and a heat dissipation material that is provided around the back-surface load material and is connected so that heat can conduct between the heat dissipation material and the heat conduction material.

JP 2015-503283 A discloses an ultrasonic probe including a heat conductor at a hole penetrating a backing material. By the conduction of heat of a piezoelectric body to a supporter of the ultrasonic probe through this heat conductor, the heat generated from the piezoelectric element can be dissipated to a structure far from the subject.

However, in the techniques as disclosed in JP 2000-184497 A and JP 2015-503283 A, the heat that has conducted to the supporter or the heat dissipation material in the ultrasonic probe is accumulated inside the ultrasonic probe. In view of this, an ultrasonic probe that can dissipate the heat generated from the ultrasonic vibrator to the structure far from the subject more efficiently so that the heat is not accumulated inside the ultrasonic probe has been desired.

SUMMARY

An object of the present invention is to provide an ultrasonic probe that can efficiently dissipate the heat that is generated from an ultrasonic vibrator and an ultrasonic diagnostic device.

To achieve the abovementioned object, according to an aspect of the present invention, an ultrasonic probe reflecting one aspect of the present invention comprises: an ultrasonic vibrator that transmits and receives an ultrasonic wave; a wire member that is electrically connected to the ultrasonic vibrator and is provided along a side surface of the ultrasonic vibrator; a shield member that is provided outside the wire member from a viewpoint of the ultrasonic vibrator and electrically protects the ultrasonic vibrator; and a first heat conduction member that is provided in contact with the ultrasonic vibrator, wherein the first heat conduction member and the shield member are thermally connected to each other.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described in detail with reference to the drawings. However, the scope of the invention is not limited to the disclosed embodiments. Note that the detailed description more than necessary, for example, the detailed description of well-known matters, the redundant description of substantially the same structure, or the like may be omitted.

The drawings that are described below or referred to in the description below are provided to help a person skilled in the art understand the present invention, and do not limit the scope of claims of the present invention.

<Structure of Ultrasonic Diagnostic Device>

Figure 1:
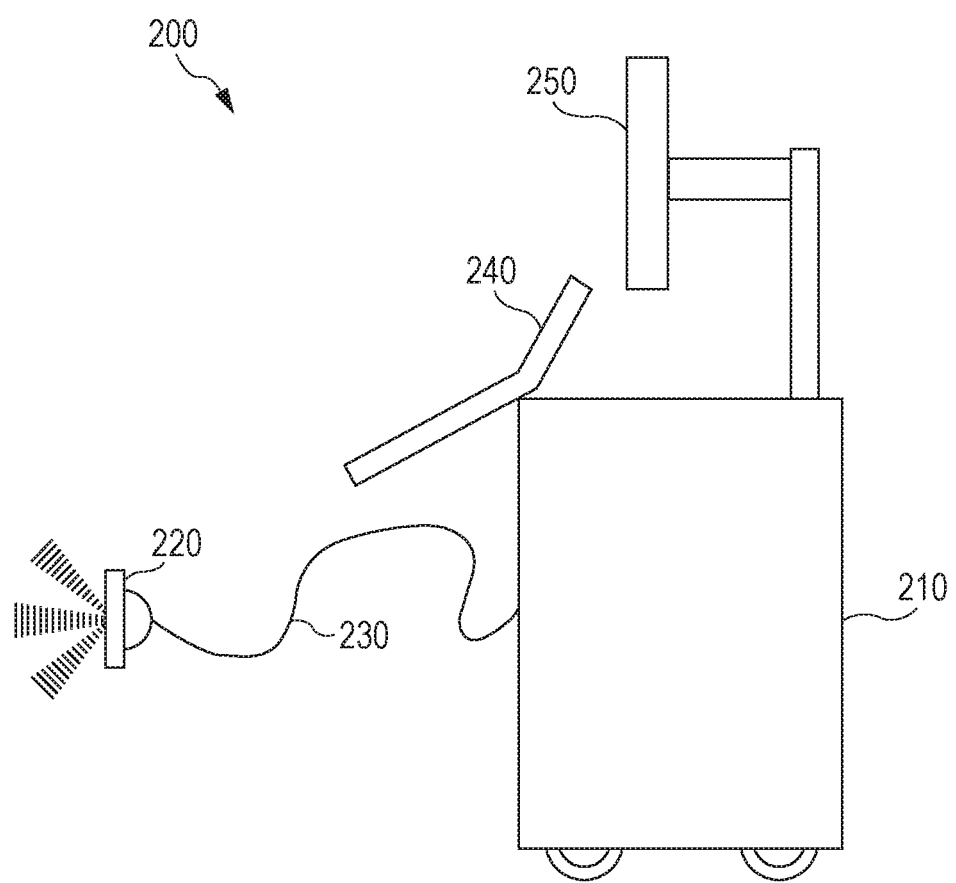
FIG. 1 is a diagram illustrating an entire structure of an ultrasonic diagnostic device.

FIG. 1 is a diagram illustrating an entire structure of an ultrasonic diagnostic device 200. As illustrated in FIG. 1, the ultrasonic diagnostic device 200 includes an ultrasonic diagnostic device main body 210, an ultrasonic probe 220, a cable 230, an operation unit 240, and a display unit 250.

The ultrasonic probe 220 transmits an ultrasonic wave (transmission ultrasonic wave) into a subject such as a living body that is not shown, and receives a reflection wave (reflection ultrasonic wave: echo) of the ultrasonic wave reflected in the subject.

The ultrasonic diagnostic device main body 210 is connected to the ultrasonic probe 220 through the cable 230, and by transmitting a driving signal of an electric signal to the ultrasonic probe 220, the ultrasonic diagnostic device main body 210 causes the ultrasonic probe 220 to transmit an ultrasonic transmission signal. Then, the ultrasonic probe 220 having received the reflection wave from the inside of the subject generates an ultrasonic reception signal, and based on the ultrasonic reception signal, the internal state of the subject is made into an ultrasonic image.

The operation unit 240 is an operation device such as a switch, a button, a keyboard, a mouse, a touch panel, or the like, and receives an operation of a doctor, a testing technician, or other people corresponding to a user of the ultrasonic diagnostic device 200.

The display unit 250 is a display device such as a liquid crystal display (LCD) or an organic EL display, and displays the ultrasonic image generated by the ultrasonic diagnostic device main body 210 or displays various display screens in accordance with the state of the ultrasonic diagnostic device 200.

Figure 2:
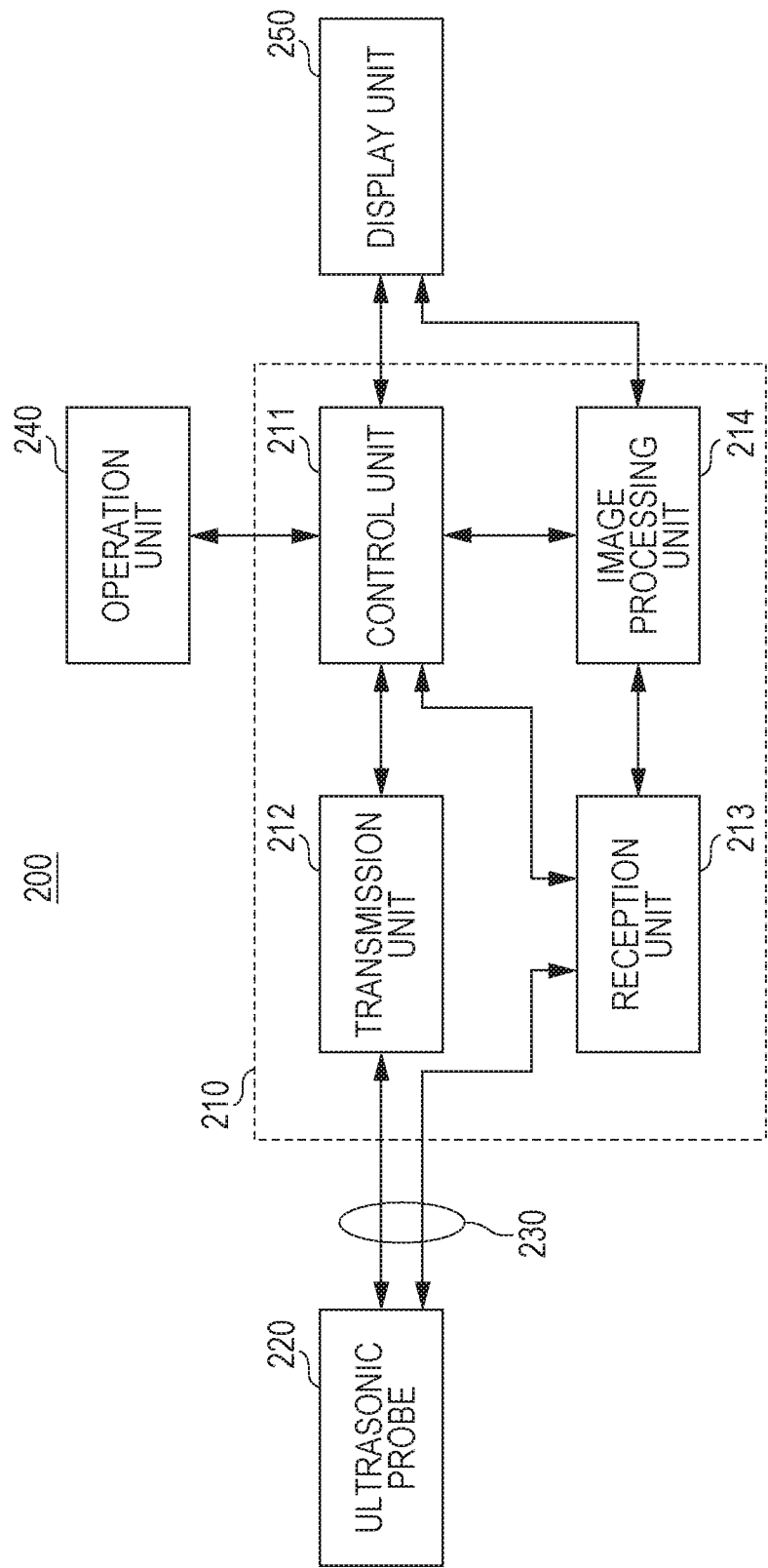
FIG. 2 is a block diagram illustrating an electric structure of the ultrasonic diagnostic device.

Next, an electric structure of the ultrasonic diagnostic device 200 is described. FIG. 2 is a block diagram illustrating an electric structure of the ultrasonic diagnostic device 200.

As illustrated in FIG. 2, the ultrasonic diagnostic device main body 210 includes a control unit 211 connected to the operation unit 240, a transmission unit 212 and a reception unit 213 that are connected to the control unit 211 and the cable 230, and an image processing unit 214 connected to each of the reception unit 213 and the control unit 211. Note that each of the control unit 211 and the image processing unit 214 is connected to the display unit 250.

The control unit 211 is a circuit that includes, for example, a microprocessor, a storage element, a peripheral circuit, and the like, and controls the entire ultrasonic diagnostic device 200 by controlling the ultrasonic probe 220, the operation unit 240, the transmission unit 212, the reception unit 213, the image processing unit 214, and the display unit 250 in accordance with their functions.

The transmission unit 212 transmits a signal from the control unit 211 to the ultrasonic probe 220, for example. The reception unit 213, for example, receives the signal from the ultrasonic probe 220 and outputs the signal to the control unit 211 or the image processing unit 214.

The image processing unit 214 is, for example, a circuit that forms an image (ultrasonic image) representing the internal state of the subject on the basis of the signal received in the reception unit 213 in accordance with the control of the control unit 211. For example, the image processing unit 214 includes a digital signal processor (DSP) that generates the ultrasonic image of the subject, and a digital-analog conversion circuit (DAC circuit) that converts a signal processed in the DSP from a digital signal to an analog signal.

For example, in the ultrasonic diagnostic device 200, the control unit 211 outputs a signal (transmission signal) to the transmission unit 212 so that the transmission unit 212 transmits an ultrasonic wave to the subject such as a living body, and moreover causes the reception unit 213 to receive an electric signal (reception signal) generated by the ultrasonic probe 220 on the basis of a reflection wave from the inside of the subject. The reception signal received in the reception unit 213 is processed into an image signal by the image processing unit 214. The image signal is transmitted to the display unit 250 and an image is displayed in the display unit 250. The display unit 250 also displays an image based on the information input from the operation unit 240 and transmitted through the control unit 211, and an operation (display of text, movement or magnification of a displayed image, or the like).

The ultrasonic diagnostic device 200 is used for a medical ultrasonic diagnostic device. The ultrasonic diagnostic device 200 is also applicable to a device that displays a search result by an ultrasonic wave in image, numeral, or the like, such as a fish finder (sonar) or a defectoscope for a non-destructive inspection.

Figure 3:
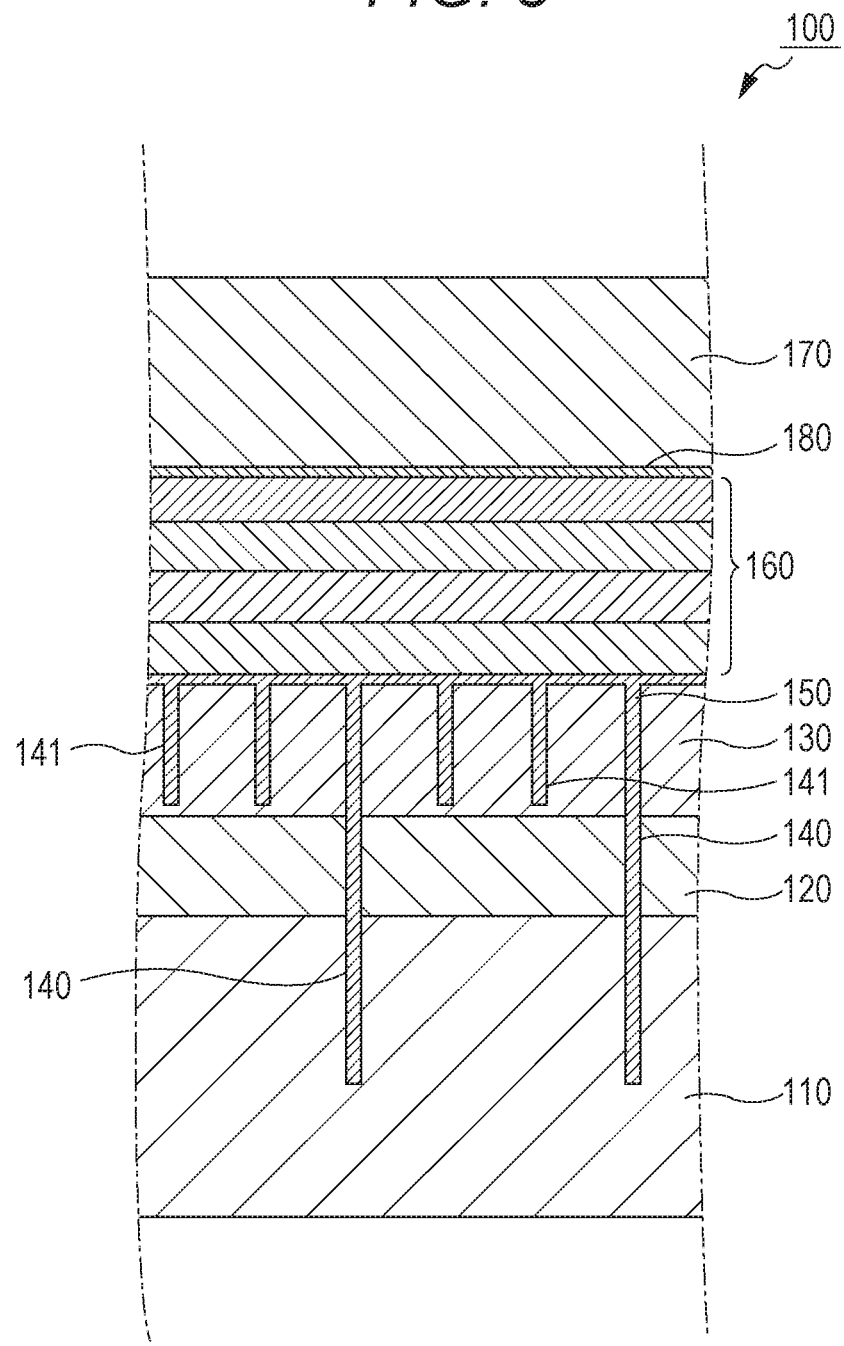
FIG. 3 is a diagram schematically illustrating a structure of an ultrasonic vibrator.

Next, the ultrasonic probe 220 is described. The ultrasonic probe 220 includes an ultrasonic vibrator 100 inside a case. First, the ultrasonic vibrator 100 is described below. FIG. 3 is a diagram schematically illustrating a structure of the ultrasonic vibrator 100. The ultrasonic vibrator 100 includes a backing layer 110, a flexible printed circuit (FPC) 120, a piezoelectric material layer 130, grooves 140 and 141, a filling material 150, an acoustic matching layer 160, an acoustic lens 170, and an adhesive layer 180.

The backing layer 110 is an ultrasonic wave absorber that supports the piezoelectric material layer 130 and absorbs the unnecessary ultrasonic wave. That is to say, the backing layer 110 is attached to a surface of the piezoelectric material layer 130 on a side opposite to a surface thereof that transmits and receives the ultrasonic wave to and from the subject (back surface: surface on the lower side in FIG. 3), and absorbs the ultrasonic wave that is generated on the opposite side in the direction of the subject.

The FPC 120 is, for example, a printed board including a pattern wire for a piezoelectric element to be described below. The FPC 120 is connected to a pair of electrodes of the piezoelectric material layer 130. The FPC 120 is one example of a wire member in the present invention. For example, the FPC 120 includes a signal leading wire serving as one electrode, and a ground leading wire to be connected to the other electrode that is not shown. The FPC 120 may be a commercial product with the appropriate pattern as described above. The FPC 120 is connected to a side surface in a longitudinal direction of the ultrasonic vibrator 100.

Moreover, an insulating layer 226 to insulate each wire of the FPC 120 from other metal members (particularly, a shield 223 to be described below) is provided (for the shield 223 and the insulating layer 226, see FIG. 5). The insulating layer 226 is formed of, for example, a material with a high insulating property such as polyimide. The material used to attach the insulating layer 226 to the FPC 120 may be, for example, epoxy resin or acrylic resin.

It is desirable that the backing layer 110 and the FPC 120 are bonded to each other with an insulating adhesive or the like.

The piezoelectric material layer 130 is a layer including a piezoelectric material and includes a pair of electrodes that is not shown. When a driving voltage (transmission signal) is applied from the ultrasonic diagnostic device main body 210, the piezoelectric material layer 130 vibrates and generates an ultrasonic wave. The piezoelectric material layer 130 receives the ultrasonic wave reflected in the subject, and converts the received ultrasonic wave into a voltage (reception signal). The ultrasonic wave generated by the piezoelectric material layer 130 is emitted from a surface of the piezoelectric material layer 130 on the acoustic matching layer 160 side (front surface: surface on the upper side in FIG. 3).

Note that in order to improve the resonance frequency characteristic of the piezoelectric material layer 130, a composite piezoelectric layer may be used as the piezoelectric material layer 130. The composite piezoelectric layer is formed by alternately disposing a piezoelectric material and a polymer material of epoxy resin or the like in a direction perpendicular to the direction where the ultrasonic wave is emitted to the subject, and integrating the piezoelectric material and the polymer material. Since the piezoelectric material and the polymer material are integrated, the composite piezoelectric layer has an electric-mechanical bonding coefficient that is approximately equal to that of the piezoelectric material, and the acoustic impedance Za of the composite piezoelectric layer can be reduced to be lower than that of the piezoelectric material. Thus, the acoustic impedance difference between the piezoelectric material layer 130 and the acoustic matching layer 160 to be described below can be reduced; therefore, the resonance frequency characteristic of the piezoelectric material layer 130 can be a wider frequency band.

The groove 140 has the depth of reaching the backing layer 110 from the surface of the piezoelectric material layer 130, and the groove 141 has the depth of reaching the piezoelectric material layer 130 from the surface of the piezoelectric material layer 130. The groove 140 sections the piezoelectric elements for every main element, and the groove 141 sections the piezoelectric element for every three sub-elements that are arranged in parallel to each other in one main element. Each of the grooves 140 and 141 is formed by a grooving process with the use of a dicing saw, for example, and has a width of, for example, 15 to 30 μm. The pitch of the main elements (center-to-center distance of grooves 140) is, for example, 0.15 to 0.30 mm, and the pitch of the sub-elements (center-to-center distance of adjacent grooves (groove 141 or 140)) is, for example, 0.05 to 0.15 mm.

The grooves 140 and 141 are filled with the filling material 150. The filling material 150 also exists between the piezoelectric material layer 130 and the acoustic matching layer 160, and its existence is emphasized in FIG. 3. Between the piezoelectric material layer 130 and the acoustic matching layer 160, actually, the filling material 150 exists with a thickness of such a degree that the filling material 150 functions as an adhesive for attaching the both to each other.

The acoustic matching layer 160 is a layer for matching the acoustic characteristics between the piezoelectric material layer 130 and the acoustic lens 170 to be described below. The ultrasonic vibrator 100 is structured so that the acoustic impedance decreases in the order of the piezoelectric material layer 130, the acoustic matching layer 160, and the acoustic lens 170. This prevents the ultrasonic wave from being reflected on the surface of the subject, and thus the sensitivity of the ultrasonic vibrator 100 can be increased. The acoustic matching layer 160 is disposed on the subject side (front surface side) of the piezoelectric material layer 130, and is, for example, disposed through the other electrode described above.

The acoustic lens 170 is a layer for focusing the ultrasonic wave emitted from the piezoelectric material layer 130. The acoustic lens 170 is formed of, for example, a soft polymer material having an intermediate acoustic impedance between the subject and the acoustic matching layer 160.

The adhesive layer 180 is, for example, a silicone adhesive layer, and attaches the acoustic matching layer 160 and the acoustic lens 170 to each other.

Although FIG. 3 does not illustrate, an acoustic reflection layer that is not shown may be disposed on a back surface of the piezoelectric material layer 130. The acoustic reflection layer is a reflection layer that reflects the ultrasonic wave generated in the piezoelectric material layer 130. One surface of the acoustic reflection layer is bonded to the back surface of the piezoelectric material layer 130, and the other surface of the acoustic reflection layer is bonded to the backing layer 110. The acoustic reflection layer reflects the ultrasonic wave, which comes from the piezoelectric material layer 130 in a direction opposite to the subject direction, to the subject direction and increases the power of the ultrasonic wave that enters the subject.

When the ultrasonic vibrator 100 as described above (particularly, piezoelectric material layer 130) generates the ultrasonic wave, the ultrasonic vibrator 100 also generates heat at the same time. When this heat conducts to the acoustic matching layer 160 and the acoustic lens 170 side, the temperature of an acoustic window 222 (see FIG. 4A) that is a part of the ultrasonic probe 220 to be in contact with the subject increases and this is not preferable. Therefore, in the ultrasonic probe 220 according to the present invention, the heat generated from the ultrasonic vibrator 100 is dissipated to the backing layer 110 on a side opposite to the acoustic window 222 from the viewpoint of the ultrasonic vibrator 100 by the use of a structure as below.

Figure 4A:
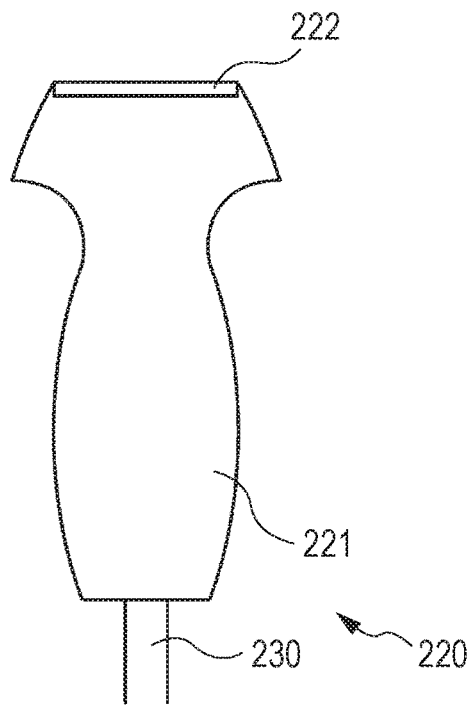
FIG. 4A is a diagram for describing an external appearance of the ultrasonic probe.

FIG. 4A is a diagram for describing an external appearance of the ultrasonic probe 220. As illustrated in FIG. 4A, the ultrasonic probe 220 includes a case 221 and the acoustic window 222. The case 221 is a member that supports an internal structure of the ultrasonic probe 220. The acoustic window 222 is a window that is in contact with the subject directly or through a coupling member for ultrasonic wave conduction or the like. Through the acoustic window 222, the ultrasonic wave from the ultrasonic vibrator 100 inside the ultrasonic probe 220 is delivered to the subject or the ultrasonic wave from the subject enters the ultrasonic probe 220.

Figure 4B:
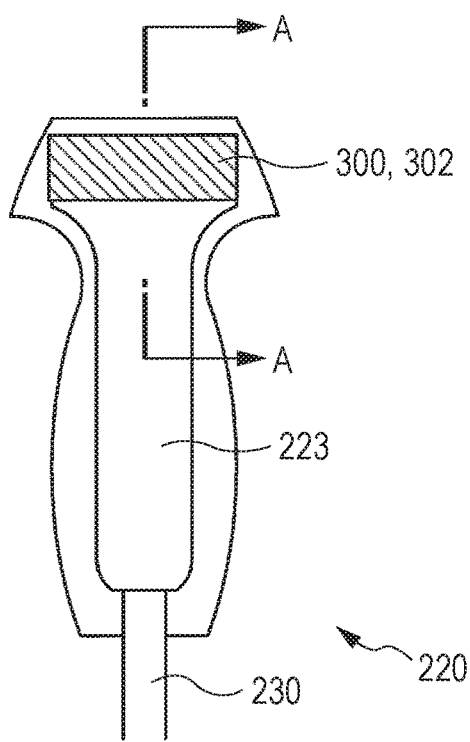
FIG. 4B is a diagram illustrating a state in which a part of a case on the front side in FIG. 4A is detached.

FIG. 4B is a diagram illustrating a state in which a part of the case 221 on the front side in FIG. 4A is detached. As illustrated in FIG. 4B, the internal structure of the ultrasonic probe 220 is covered with the shield 223.

The shield 223 is provided to reduce the coupling of an electric wave, an electromagnetic field, and an electrostatic field, and to cover the ultrasonic vibrator 100. Actually, the shield 223 is formed to have a sheet-like shape whose width is larger than the length of the case 221 in the width direction illustrated in FIG. 4B (left-right direction in FIG. 4B) (see FIG. 8 to be described below), and FIG. 4B illustrates the shield 223 that is folded after covering the internal structure of the ultrasonic probe 220. Note that the width direction of the case 221 corresponds to the longitudinal direction of the ultrasonic vibrator 100.

The shield 223 is fixed to the FPC 120 through the insulating layer 226 by the use of, for example, a double-sided tape or a non-conductive adhesive. The shield 223 is sealed by solder, a conductive adhesive, or the like so that a space is not formed when the shield 223 is folded. Although not shown, the shield 223 is connected to a GND signal line, and prevents the entry or leakage of the electric wave, the electromagnetic field, the electrostatic field, and the like from the inside of the shield 223. The shield 223 is formed of, for example, a metal foil of copper, nickel, or the like.

Furthermore, as illustrated in FIG. 4B, the ultrasonic probe 220 includes a first heat conduction structure 300 for conducting and dissipating the heat generated from the ultrasonic vibrator 100. The details of the first heat conduction structure 300 will be described below.

In the description below, for convenience, an upward direction in FIG. 4A and FIG. 4B is defined as an upward direction of the ultrasonic probe 220, and a downward direction in FIG. 4A and FIG. 4B is defined as a downward direction of the ultrasonic probe 220. As described above, a left-right direction in FIG. 4A and FIG. 4B corresponding to the width direction of the case 221 corresponds to the longitudinal direction of the ultrasonic probe 220 and the ultrasonic vibrator 100.

Figure 5:
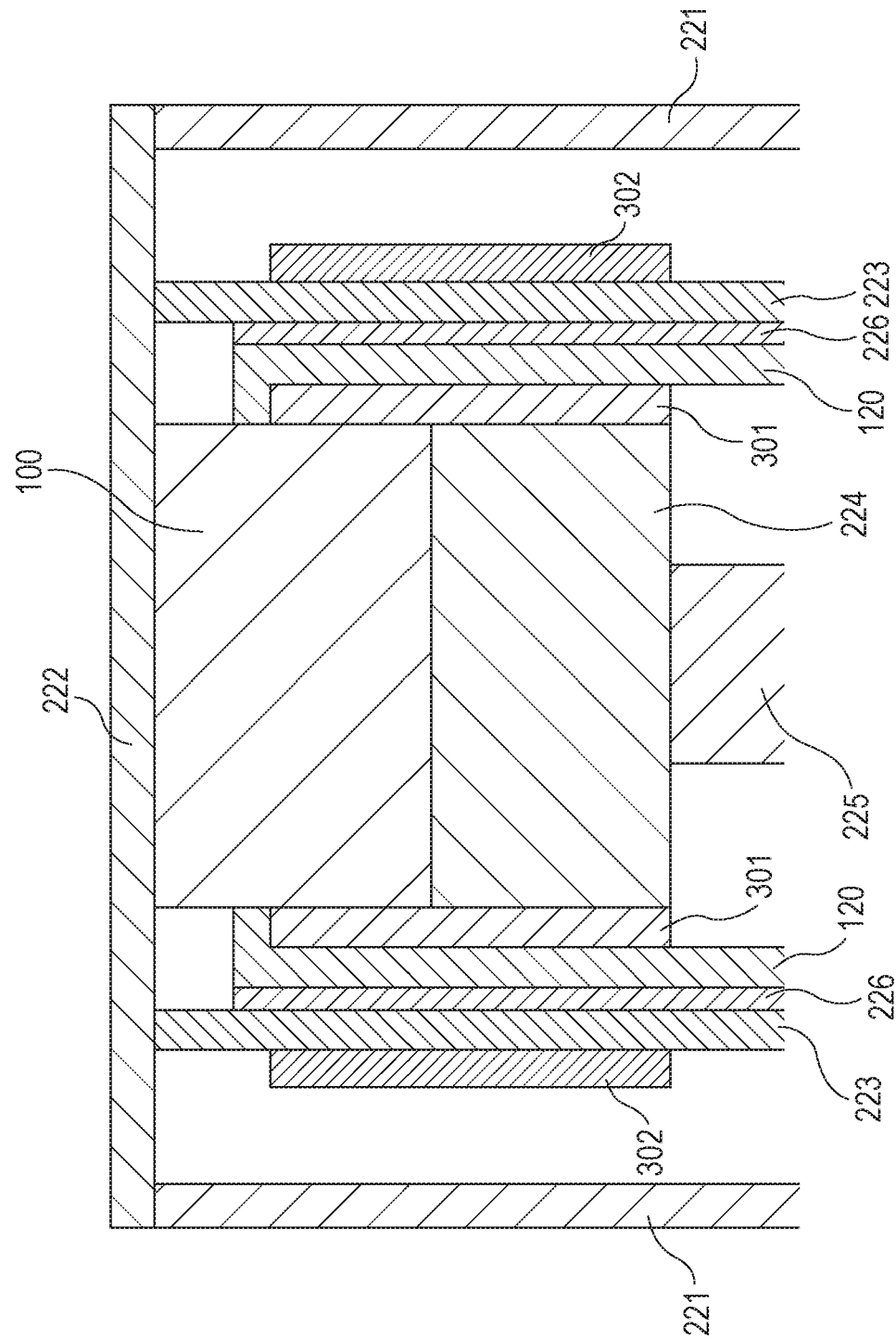
FIG. 5 is a diagram for describing an internal structure of the ultrasonic probe.

FIG. 5 is a cross-sectional view taken along a line A-A of FIG. 4B for describing the internal structure of the ultrasonic probe 220. That is to say, FIG. 5 is a cross-sectional view taken along a short-side direction of the ultrasonic probe 220 (depth direction on a paper surface in FIG. 4B). Note that the thickness, the size, and the like of each component are exaggerated in FIG. 5 in order to clarify the internal structure of the ultrasonic probe 220. As illustrated in FIG. 5, the ultrasonic vibrator 100 is supported by a stay 224.

The stay 224 is a base member that supports the ultrasonic vibrator 100. The stay 224 is an example of a base member in the present invention. A surface of the stay 224 opposite to a surface thereof that supports the ultrasonic vibrator 100 is bonded to a support member 225. A part of the ultrasonic vibrator 100 that is in contact with the stay 224 is the backing layer 110 described above. The stay 224 is desirably formed of a material with a relatively high heat conduction property. Specifically, the stay 224 is formed of, for example, metal, epoxy resin, phenolic resin, or the like.

A surface of the ultrasonic vibrator 100 opposite to a surface thereof that is supported by the stay 224 is provided with the acoustic window 222. In FIG. 5, an upper surface of the ultrasonic vibrator 100, that is, a part where the acoustic lens 170 exists is in contact with the acoustic window 222; however, between the acoustic lens 170 and the acoustic window 222, a space that is closed by a part of the case 221, for example, and filled with a coupling solution or the like may be provided.

In the above description, the ultrasonic probe 220 includes the acoustic window 222 through which the ultrasonic probe 220 is in contact with the subject; however, the present invention is not limited to this example. That is to say, the ultrasonic probe 220 does not need to include the acoustic window 222 and the acoustic lens 170 may be brought into contact with the subject directly.

As illustrated in FIG. 5, the FPC 120 is provided to extend to a direction of the stay 224 along a side surface of the ultrasonic vibrator 100 (downward direction of the ultrasonic probe 220). Although FIG. 5 does not illustrate completely, a wire of the FPC 120 is connected to a signal line housed in the cable 230 at a lower end of the FPC 120 that is not shown. This enables the FPC 120 to transmit the transmission signal from the ultrasonic diagnostic device main body 210 to the ultrasonic vibrator 100 through the cable 230, and transmit the reception signal generated by the ultrasonic probe 220 to the ultrasonic vibrator 100.

Between the FPC 120 and the shield 223, the insulating layer 226 is provided. The FPC 120 and the insulating layer 226 are attached to each other with an insulating adhesive or the like, and the insulating layer 226 and the shield 223 are attached to each other with an insulating adhesive or the like.

The shield 223 is provided to cover the entire ultrasonic vibrator 100 as described above. The shield 223 is attached to the FPC 120 through the insulating layer 226.

As illustrated in FIG. 5, a first heat conduction member 301 is provided between the FPC 120, and the stay 224 and other components of the ultrasonic vibrator 100 (in particular, the piezoelectric material layer 130 described above). That is to say, the first heat conduction member 301 is in contact with, preferably in close contact with, the ultrasonic vibrator 100 (particularly, piezoelectric material layer 130) and the stay 224. Thus, the heat generated from the ultrasonic vibrator 100 when the ultrasonic wave is transmitted conducts to the first heat conduction member 301 directly or through the stay 224. Further on the outside of the shield 223 from the viewpoint of the ultrasonic vibrator 100, a second heat conduction member 302 is provided.

The first heat conduction member 301 and the second heat conduction member 302 constitute a part of the first heat conduction structure 300, and serve to dissipate the heat generated from the ultrasonic vibrator 100 to the outside. Here, the outside refers to the outside of the case 221 in a direction opposite to the acoustic lens 170 from the viewpoint of the ultrasonic vibrator 100.

Figure 6A:
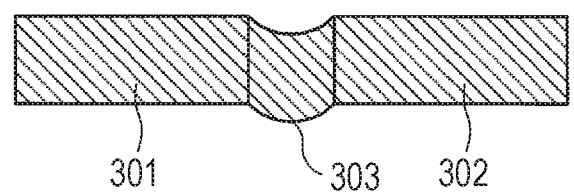
FIG. 6A is a diagram for describing a first heat conduction member, a second heat conduction member, and a connection member.
Figure 6B:
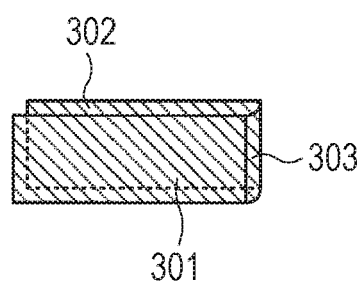
FIG. 6B is a diagram for describing the first heat conduction member, the second heat conduction member, and the connection member.

The first heat conduction member 301 and the second heat conduction member 302 are connected through a connection member 303 illustrated in FIG. 6A and FIG. 6B. FIG. 6A and FIG. 6B are diagrams for describing the first heat conduction member 301, the second heat conduction member 302, and the connection member 303. FIG. 6A is a diagram representing a connection relation among the first heat conduction member 301, the second heat conduction member 302, and the connection member 303, in which the first heat conduction member 301, the second heat conduction member 302, and the connection member 303 are extracted from the ultrasonic probe 220 and opened. In FIG. 6A, the size of the connection member 303 is exaggerated for the description.

Here, the first heat conduction member 301, the second heat conduction member 302, and the connection member 303 are components included in the first heat conduction structure 300 described above.

As illustrated in FIG. 6A, the first heat conduction member 301 and the second heat conduction member 302 are formed to have, for example, a rectangular shape. When the first heat conduction member 301 and the second heat conduction member 302 are attached to the ultrasonic probe 220, the first heat conduction member 301 and the second heat conduction member 302 are attached so that the long-side direction of the rectangular shape coincides with the longitudinal direction of the ultrasonic probe 220. In FIG. 4B described above, the second heat conduction member 302 as the heat conduction member on the outside is illustrated.

The width of the connection member 303 is substantially equal to the short side of the first heat conduction member 301 and the second heat conduction member 302, and the connection member 303 connects between the short side of the first heat conduction member 301 and the short side of the second heat conduction member 302. This enables the connection member 303 to connect between the first heat conduction member 301 and the second heat conduction member 302 thermally and physically. Thus, the heat generated from the ultrasonic vibrator 100 conducts from the first heat conduction member 301 to the second heat conduction member 302 through the connection member 303.

The first heat conduction member 301, the second heat conduction member 302, and the connection member 303 are formed of a material with a high heat conduction property. Specifically, the first heat conduction member 301, the second heat conduction member 302, and the connection member 303 may be formed of a sheet of copper, aluminum, carbon fiber, graphite, graphene, or the like. It is particularly preferable that the first heat conduction member 301, the second heat conduction member 302, and the connection member 303 are formed of a flaky graphite crystal with a thickness of 1 to 100 nm as described in JP 2016-130212 A. Although the first heat conduction member 301, the second heat conduction member 302, and the connection member 303 may be formed of different materials, these members are preferably formed of the same material.

The first heat conduction member 301, the second heat conduction member 302, and the connection member 303, particularly the connection member 303, have plasticity. Therefore, the first heat conduction member 301 and the second heat conduction member 302 can face each other as illustrated in FIG. 5 and FIG. 6B while being connected by the connection member 303 thermally and physically. FIG. 6B illustrates a state in which the first heat conduction member 301 and the second heat conduction member 302 face each other by the bending of the connection member 303.

In the above description, the first heat conduction member 301, the second heat conduction member 302, and the connection member 303 are separate bodies; however, these members may be integrated. Even when the first heat conduction member 301, the second heat conduction member 302, and the connection member 303 are integrated, the first heat conduction member 301 part and the second heat conduction member 302 part can be disposed to face each other as illustrated in FIG. 6B because these materials have plasticity.

Figure 7:
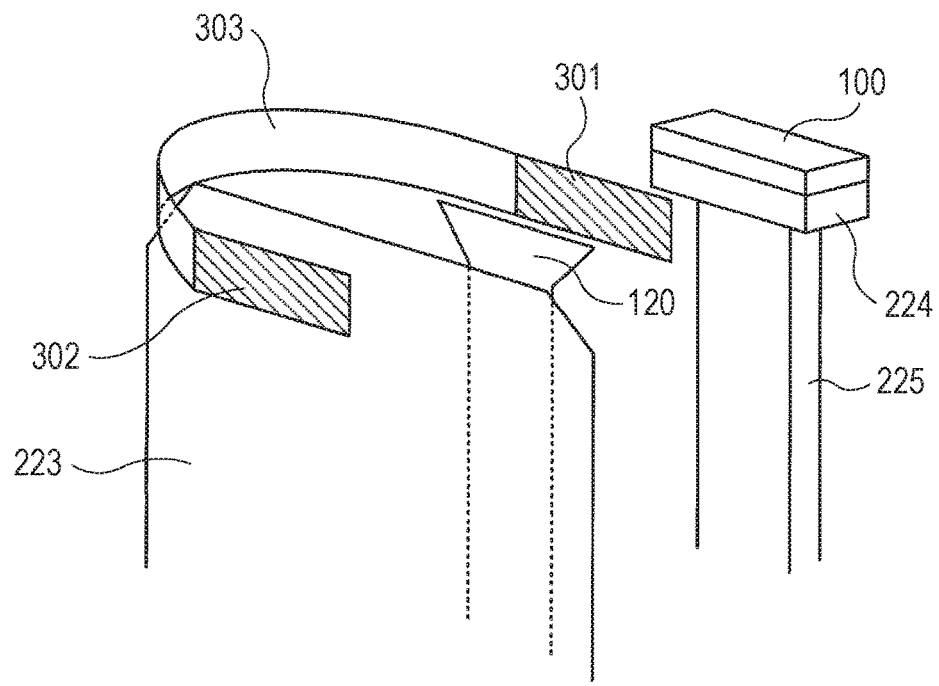
FIG. 7 is an exploded perspective view of the internal structure of the ultrasonic probe.

FIG. 7 is an exploded perspective view of the internal structure of the ultrasonic probe 220. In FIG. 7, the ultrasonic probe 220 is exploded into components, and the components are separated along the short-side direction of the ultrasonic vibrator 100 and shown. Although FIG. 7 illustrates the components separated from each other, the FPC 120 is provided to the side surface in the longitudinal direction of the ultrasonic vibrator 100, and the first heat conduction member 301 is provided between the ultrasonic vibrator 100 and the stay 224, and the FPC 120 (see FIG. 5). The FPC 120 and the shield 223 are fixed through the insulating layer 226 (not shown in FIG. 7), and the second heat conduction member 302 is provided outside the shield 223. In FIG. 7, the length of the connection member 303 (width in a direction perpendicular to the short-side direction of the first heat conduction member 301 and the second heat conduction member 302) is exaggerated, and the first heat conduction member 301 and the second heat conduction member 302 are connected to each other by the connection member 303. Actually, the length of the connection member 303 may be substantially the same as the total thickness of the FPC 120, the insulating layer 226, and the shield 223.

For simplicity, FIG. 7 illustrates only the structure that is provided on one side surface side in the longitudinal direction of the ultrasonic vibrator 100; however, the similar structure is provided also on the opposite side surface actually (see FIG. 5).

Figure 8:
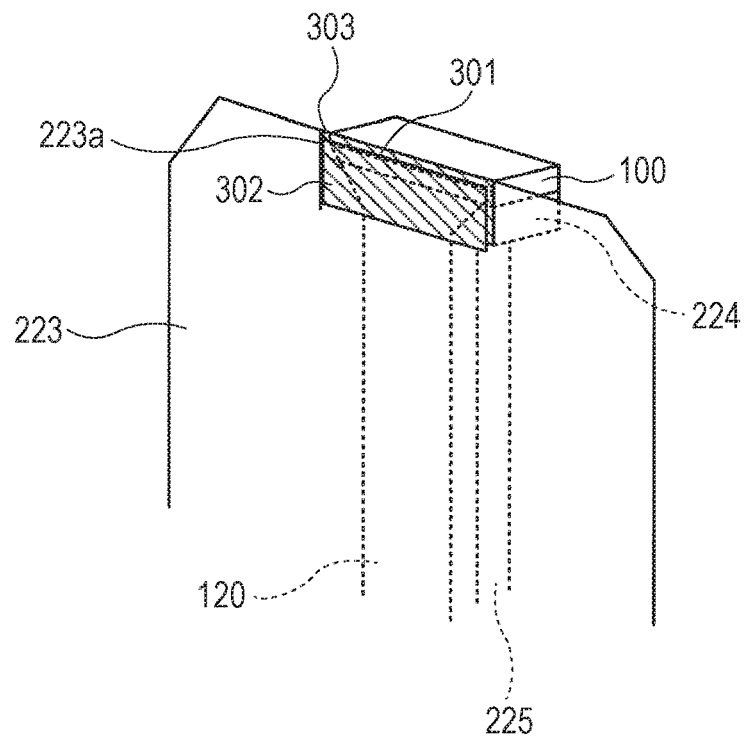
FIG. 8 is a perspective view illustrating a state in which the internal structure of the ultrasonic probe illustrated in FIG. 7 is combined.

FIG. 8 is a perspective view illustrating a state in which the internal structure of the ultrasonic probe 220 illustrated in FIG. 7 is combined. The shield 223 illustrated in FIG. 8 is folded so as to cover the ultrasonic vibrator 100, the FPC 120, the stay 224, and the support member 225 and put into the case 221; then, a state illustrated in FIG. 4B is obtained. Note that as illustrated in FIG. 8, the shield 223 includes a cut 223a for passing the connection member 303. The cut 223a is sealed by solder, a conductive adhesive, or the like so that, when the shield 223 is folded, a gap is not formed between the connection member 303 and the shield 223. Note that, for simplicity, FIG. 8 illustrates only the structure that is provided on one side surface side in the longitudinal direction of the ultrasonic vibrator 100; however, the similar structure is provided also on the opposite side surface actually (see FIG. 5).

Although the shield 223 covers the entire ultrasonic vibrator 100, the FPC 120, the stay 224, and the support member 225 in FIG. 8, it is not always necessary that the shield 223 covers the entire ultrasonic vibrator 100. That is to say, the shield 223 may have a structure in which, for example, the shield 223 covers only a part of the ultrasonic vibrator 100 below the wiring part of the FPC 120. In this case, even if the cut 223a is not provided to the shield 223, the second heat conduction member 302 can be brought into contact with the shield 223 by bending the connection member 303.

Then, the second heat conduction member 302 can be provided in contact with, more preferably in close contact with, an external surface of the shield 223.

By the first heat conduction structure 300 as above, the heat generated from the ultrasonic vibrator 100 conducts to the outside as described below. That is to say, when the ultrasonic vibrator 100 generates heat, the heat conducts from the ultrasonic vibrator 100 directly or through the stay 224 to the first heat conduction member 301 provided in contact with the ultrasonic vibrator 100 and the stay 224 (see FIG. 5 and FIG. 8).

Since the first heat conduction member 301 is thermally connected to the second heat conduction member 302 through the connection member 303 as illustrated in FIG. 6A and FIG. 7, for example, the heat having conducted to the first heat conduction member 301 conducts to the second heat conduction member 302 through the connection member 303. Then, since the second heat conduction member 302 is provided in contact with the shield 223, the heat having conducted to the second heat conduction member 302 conducts to the shield 223. The shield 223 has an area large enough to cover the internal structure of the ultrasonic probe 220 including a lower part of the ultrasonic probe 220 as illustrated in FIG. 4B. Therefore, the heat having conducted to the shield 223 diffuses to the air, for example, as appropriate. This can prevent the situation that the heat generated from the ultrasonic vibrator 100 increases the temperature of the part of the ultrasonic probe to be in contact with the subject (acoustic window 222 or acoustic lens 170) to make the subject feel uncomfortable.

Here, in order to diffuse the heat generated from the ultrasonic vibrator 100 more appropriately, the area where the second heat conduction member 302 is in contact with the shield 223 may be larger than the area where the first heat conduction member 301 is in contact with the ultrasonic vibrator 100 and the stay 224. This structure can be achieved by, for example, forming the second heat conduction member 302 to be a larger area than the first heat conduction member 301. Alternatively, since the area of a side surface part of the ultrasonic vibrator 100 and the stay 224 in the longitudinal direction is smaller than the area of the shield 223, the above structure can be achieved also when the area of the first heat conduction member 301 and the second heat conduction member 302 is larger than the area of the side surface part of the ultrasonic vibrator 100 and the stay 224 in the longitudinal direction.

Figure 9:
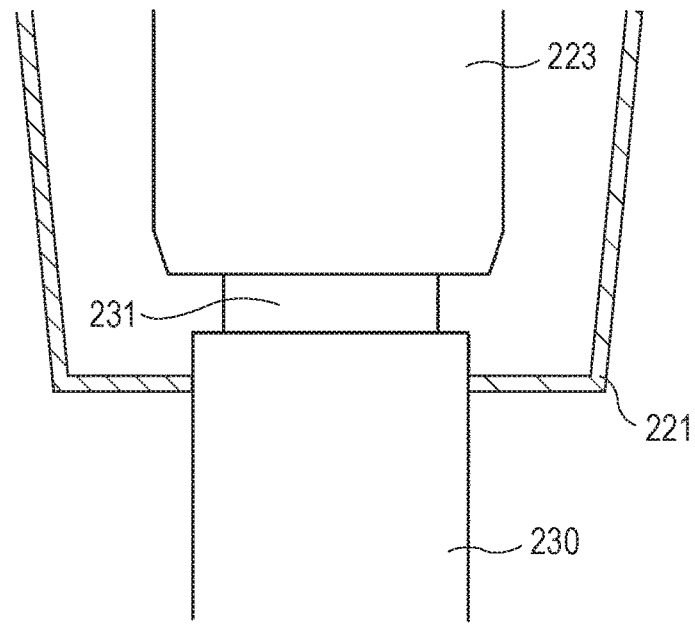
FIG. 9 is a diagram illustrating a state in which a lower end part of a shield is connected to a covering material in a cable.

In addition, when a lower end part of the shield 223 is connected to a covering material 231 that covers the signal line provided in the cable 230 as illustrated in FIG. 9, the heat having conducted to the shield 223 diffuses more appropriately. FIG. 9 is a diagram illustrating a state in which the lower end part of the shield 223 is connected to the covering material 231 in the cable 230.

In FIG. 9, the covering material 231 in the cable 230 is thermally connected to the shield 223 in the case 221. In FIG. 9, the shield 223 is folded as illustrated in FIG. 4B. In FIG. 9, the covering material 231 of the cable 230 is exposed to the outside of the cable 230 in the case 221; however, the present invention is not limited to this structure, and for example, the lower end part of the shield 223 may enter the cable 230 and be connected to the covering material 231.

<Operation and Effect>

As described above, the ultrasonic probe 220 according to the present invention includes: the ultrasonic vibrator 100; the FPC (wire member) 120 that is electrically connected to the ultrasonic vibrator 100 and is provided along the side surface of the ultrasonic vibrator 100 in the longitudinal direction; the shield 223 that is attached to the outside of the FPC 120 from the viewpoint of the ultrasonic vibrator 100 and electrically protects the ultrasonic vibrator 100; the first heat conduction member 301 that is provided between the FPC 120 and the ultrasonic vibrator 100 in contact with the ultrasonic vibrator 100; the second heat conduction member 302 that is provided outside the shield 223 in contact with the shield 223; and the connection member 303 that thermally connects between the first heat conduction member 301 and the second heat conduction member 302.

By such a structure, the heat generated from the ultrasonic vibrator 100 conducts to the first heat conduction member 301, and then to the second heat conduction member 302 through the connection member 303. Since the second heat conduction member 302 is provided in contact with the shield 223, the heat having conducted to the second heat conduction member 302 conducts to the shield 223. Thus, the amount of heat to conduct from the ultrasonic vibrator 100 to a contact part in contact with the subject (acoustic window 222 or acoustic lens 170) is reduced. This can prevent the situation that the subject who gets in contact with the contact part with high temperature feels uncomfortable.

In order to briefly describe an effect of the first heat conduction structure 300 in the ultrasonic probe 220 according to the present invention, description will be made of results of simulating the temperatures in the contact part in a case where the first heat conduction structure 300 is provided and in a case where the first heat conduction structure 300 is not provided with reference to Table 1.

TABLE 1

| | Temperature of contact part | | Reduced temperature effect |
|---|---|---|---|
| | Unused ° C. | Used ° C. | ° C. |
| Graphene | 40.7 | 33.4 | 7.3 |
| Copper | | 35.0 | 5.7 |
| Aluminum | | 35.5 | 5.2 |

The left column in Table 1 shows the materials of the first heat conduction structure 300. In Table 1, "used" corresponds to the case where the first heat conduction structure 300 is provided as described in the above embodiment and "unused" corresponds to the case where the first heat conduction structure 300 is not provided.

The material of the FPC 120 has a lower heat conductive property than that of the first heat conduction structure 300, and the insulating layer 226 whose heat conduction property is relatively low is provided between the shield 223 and the FPC 120. Therefore, when the first heat conduction structure 300 is not provided, the heat generated from the ultrasonic vibrator 100 does not conduct to the shield 223 and mostly conducts to the contact part side; thus, the temperature in the contact part increases.

On the other hand, in the case where the first heat conduction structure 300 is provided as described in the above embodiment, the heat generated from the ultrasonic vibrator 100 conducts to the shield 223; therefore, the temperature of the contact part can be reduced to be lower than the temperature in the case where the first heat conduction structure 300 is not provided as shown in Table 1.

<Modifications>

The embodiment according to the present invention has been described with reference to the drawings; however, the present invention is not limited to the above example. Various changes and modifications that can be conceived by a person skilled in the art within the range described in the scope of claims are also included in the technical range of the present invention. In addition, the components in the above embodiment can be combined arbitrarily within the range not departing from the concept of the disclosure.

[First Modification]

In the embodiment described above, the first heat conduction member 301 provided inside the FPC 120, the insulating layer 226, and the shield 223, and the second heat conduction member 302 provided outside the shield 223 are connected to each other thermally and physically by the connection member 303 that detours around the FPC 120.

In the first modification, for example, the FPC 120, the insulating layer 226, and the shield 223 may be provided with a hole, and the first heat conduction member 301 and the second heat conduction member 302 may be connected by passing the connection member 303 through the hole. This hole is provided avoiding the wire of the FPC 120. After the connection member 303 is inserted into this hole, the hole is sealed by solder, a conductive adhesive, or the like in order for the shield 223 to keep protecting the internal structure of the ultrasonic vibrator 100 electrically. The number of holes to pass the connection member 303 is not limited to one and may be more than one. The shape of the hole is not limited to a particular shape in the present invention, and may be any shape.

[Second Modification]

In the embodiment described above, the heat generated from the ultrasonic vibrator 100 conducts to the shield 223 through the first heat conduction structure 300; however, the heat may be diffused through the support member 225, which will be described below.

Figure 10:
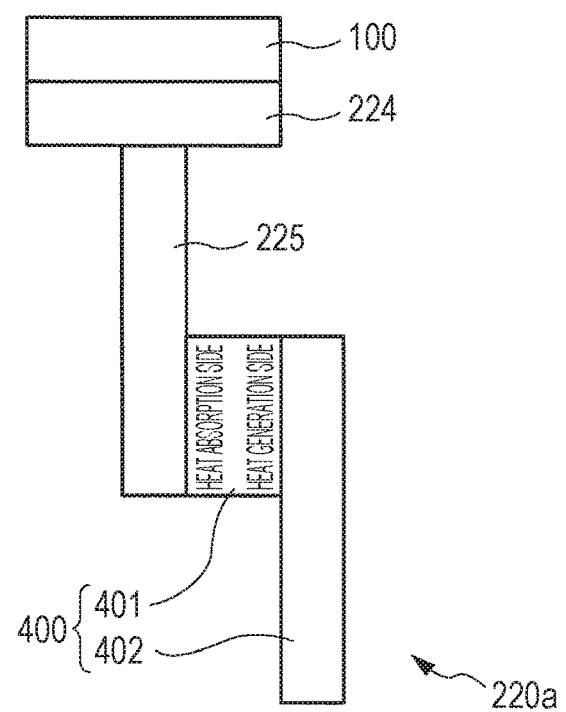
FIG. 10 is a diagram for describing an internal structure of an ultrasonic probe according to a second modification.

FIG. 10 is a diagram for describing an internal structure of an ultrasonic probe 220a according to a second modification. In the second modification, the ultrasonic vibrator 100, the stay 224, and the support member 225 have the structures similar to those of the above embodiment as illustrated in FIG. 10, and the other structures are not illustrated. As illustrated in FIG. 10, in the second modification, a second heat conduction structure 400 including a Peltier element 401 and a third heat conduction member 402 is provided at a lower end part of the support member 225.

The Peltier element 401 is an element (thermoelectric element) that transfers heat from a heat absorption side to a heat generation side by the supply of current. The heat absorption side of the Peltier element 401 is connected to the support member 225 and the heat generation side thereof is connected to the third heat conduction member 402.

In such a structure, the heat generated from the ultrasonic vibrator 100 conducts to the stay 224 with a relatively high heat conduction property, and then to the support member 225. Therefore, in the present second modification, the support member 225 is formed of a material with a relatively high heat conduction property, such as metal.

The Peltier element 401 absorbs and generates heat by using a part of the transmission signals transmitted from the ultrasonic diagnostic device main body 210 through the cable 230. That is to say, the Peltier element 401 absorbs the heat, which has conducted to the support member 225, from the heat absorption side and conducts the heat to the third heat conduction member 402 connected to the heat generation side.

The third heat conduction member 402 is formed of a material with a relatively high heat conduction property, and the conducted heat can be efficiently diffused in the air or the like. Alternatively, when the third heat conduction member 402 is connected to the covering material that covers the signal line provided in the cable 230, for example, the conducted heat can be dissipated to the outside of the ultrasonic probe 220 more appropriately.

In order to improve the efficiency of the Peltier element 401, the heat conduction property of the third heat conduction member 402 is desirably higher than that of the stay 224 or the support member 225. This is because, in the general Peltier elements, the heat generation effect on the heat generation side is higher than the heat absorption effect on the heat absorption side.

In the ultrasonic probe 220a according to the second modification with such a structure, the heat generated from the ultrasonic vibrator 100 can be dissipated efficiently to the outside of the ultrasonic probe 220a.

Note that although not shown in FIG. 10 or not described in the second modification, the structure (first heat conduction structure 300) according to the above embodiment described with reference to FIG. 4A to FIG. 8 may be provided. In this case, the heat generated from the ultrasonic vibrator 100 can be dissipated efficiently to the outside of the ultrasonic probe 220 more appropriately.

The present invention is suitably applied to the ultrasonic probe in which the ultrasonic vibrator generates heat.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasonic probe comprising:
an ultrasonic vibrator that transmits and receives an ultrasonic wave;
a wire member that is electrically connected to the ultrasonic vibrator and is provided along a side surface of the ultrasonic vibrator;
a shield member that is provided outside the wire member from a viewpoint of the ultrasonic vibrator and electrically protects the ultrasonic vibrator; and
a first heat conduction member that includes a first surface directly disposed on the ultrasonic vibrator and a second surface opposite the first surface and directly disposed on the wire member such that the ultrasonic vibrator and the wire member overlap each other,
wherein the first heat conduction member and the shield member are thermally connected to each other,
wherein the first heat conduction member is provided between the wire member and the ultrasonic vibrator,
the ultrasonic probe further includes a second heat conduction member provided outside the shield member in direct contact with the shield member,
a connection member that directly connects the first heat conduction member to the second heat conduction member, both physically and thermally, and
the first head conduction member, the connection member and the second heat conduction member define a C-shaped element.

2. The ultrasonic probe according to claim 1,
wherein the first heat conduction member, the second heat conduction member, and the connection member are formed of at least any of materials including copper, aluminum, carbon fiber, graphite, and graphene.

3. The ultrasonic probe according to claim 1, further comprising:
a base member that serves as a base for the ultrasonic vibrator,
wherein the first heat conduction member is provided in contact with the ultrasonic vibrator and the base member.

4. The ultrasonic probe according to claim 3,
wherein an area where the second heat conduction member is in contact with the shield member is larger than an area where the first heat conduction member is in contact with the ultrasonic vibrator and the base member.

5. The ultrasonic probe according to claim 1, further comprising:
a cable that incorporates a signal line that is electrically connected to the wire member at an end of the ultrasonic probe on a side opposite to a side thereof where the ultrasonic vibrator is provided,
wherein the shield member is provided extending to the end of the ultrasonic probe on the side opposite to the side where the ultrasonic vibrator is provided, and
an end of the shield member is thermally connected to a covering material that covers the signal line in the cable.

6. An ultrasonic diagnostic device comprising:
the ultrasonic probe according to claim 1; and
an ultrasonic diagnostic device main body that causes the ultrasonic probe to transmit an ultrasonic transmission signal to a subject, and generates an ultrasonic image on the basis of an ultrasonic reception signal generated by the ultrasonic probe that has received a reflection wave from the subject.

* * * * *